US006956053B2

United States Patent
McDonald et al.

(10) Patent No.: US 6,956,053 B2
(45) Date of Patent: Oct. 18, 2005

(54) PYRAZOLE DERIVATIVES AND THEIR USE AS GASTRIN AND CHOLECYSTOKIN RECEPTOR LIGANDS

(75) Inventors: Iain Mair McDonald, London (GB); Caroline Minli Rachel Low, London (GB); Katherine Isobel Mary Steel, London (GB); John Spencer, London (GB)

(73) Assignee: The James Black Foundation Limited, London (GB)

( * ) Notice: Subject to any disclaimer, the term of this patent is extended or adjusted under 35 U.S.C. 154(b) by 175 days.

(21) Appl. No.: 10/275,614

(22) PCT Filed: May 4, 2001

(86) PCT No.: PCT/GB01/01976

§ 371 (c)(1),
(2), (4) Date: Apr. 23, 2003

(87) PCT Pub. No.: WO01/90078

PCT Pub. Date: Nov. 29, 2001

(65) Prior Publication Data

US 2003/0207874 A1 Nov. 6, 2003

(30) Foreign Application Priority Data

May 8, 2000 (GB) .......................................... 00114095

(51) Int. Cl.[7] ..................... A61K 31/415; C07D 231/10
(52) U.S. Cl. .................................... 514/406; 548/374.1
(58) Field of Search ........................ 514/406; 548/374.1

(56) References Cited

U.S. PATENT DOCUMENTS

| | | | |
|---|---|---|---|
| 4,670,460 A | | 6/1987 | Mardin et al. |
| 5,202,344 A | | 4/1993 | Becker et al. |
| 5,300,514 A | * | 4/1994 | Brown et al. ................ 514/314 |
| 5,314,886 A | * | 5/1994 | Becker et al. ......... 514/252.05 |
| 5,399,565 A | * | 3/1995 | Greenwood et al. ........ 514/314 |
| 5,643,926 A | * | 7/1997 | Brown et al. ................ 514/314 |

FOREIGN PATENT DOCUMENTS

| | | |
|---|---|---|
| DE | 23 63 139 | 7/1975 |
| EP | 0 467 614 A1 | 1/1992 |
| FR | 2 773 153 | 7/1999 |
| WO | WO 00/27823 | 5/2000 |

OTHER PUBLICATIONS

Wolfgang Sucrow, Einige Produkte aus 1 Alkyl 5 hydroxy–3–pyrazolcarbonsaure–methlestern, Chem. Ber 109, 261–267 (1976).

Susan E. Gibson et al., "Incorporation of Conformationally Constrained Phenylalanine Derivatives Tic, Sic, Hic and Nic Into A Cholecystokinin–B/Gastrin Receptor Antagonist", Bioorganic & Medicinal Chemistry Letters, 1997, pp. 1289–1292, vol. 7, No. 10. Pergamon.

* cited by examiner

*Primary Examiner*—Deborah C. Lambkin
(74) *Attorney, Agent, or Firm*—Heller Ehrman LLP

(57) ABSTRACT

Compounds of formula (I), (IIa) or (IIb) wherein $R^1$–$R^6$, Z, Q and n are as defined in claim 1 and their pharmaceutically acceptable salts are ligands at gastrin and/or cholecystokinin receptors. Compositions comprising a compound of formula (I), (IIa) or (IIb) are also described.

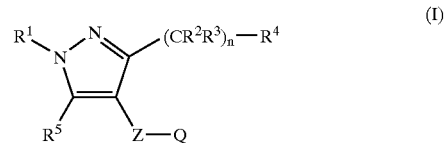

(I)

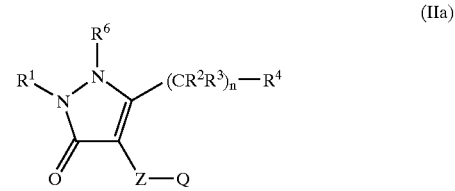

(IIa)

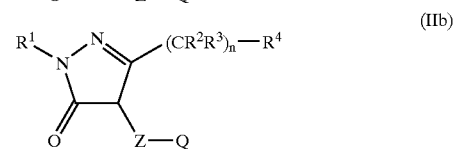

(IIb)

40 Claims, No Drawings

PYRAZOLE DERIVATIVES AND THEIR USE AS GASTRIN AND CHOLECYSTOKIN RECEPTOR LIGANDS

This application is the national phase under 35 U.S.C. § 371 of PCT International Application No. PCT/GB01/01976 which has an International filing date of May 4, 2001, the disclosure of which is incorporated herein by reference in its entirety.

This invention relates to gastrin and cholecystokinin (CCK) receptor ligands. (The receptor previously known as the $CCK_B$/gastrin receptor is now termed the $CCK_2$ receptor). The invention also relates to methods for preparing such ligands and to compounds which are useful intermediates in such methods. The invention further relates to pharmaceutical compositions comprising such ligands and methods for preparing such pharmaceutical compositions.

Gastrin and the cholecystokinins are structurally related neuropeptides which exist in gastrointestinal tissue and the central nervous system (Mutt V., *Gastrointestinal Hormones*, Glass G. B. J., ed., Raven Press, New York, p. 169; Nisson G., ibid., p. 127).

Gastrin is one of the three primary stimulants of gastric acid secretion. Several forms of gastrin are found including 34-, 17- and 14-amino acid species with the minimum active fragment being the C-terminal tetrapeptide (TrpMetAspPhe-$NH_2$) which is reported in the literature to have full pharmacological activity (Tracey H. J. and Gregory R. A., *Nature* (London), 1964, 204, 935). Much effort has been devoted to the synthesis of analogues of this tetrapeptide (and the N-protected derivative Boc-TrpMetAspPhe-$NH_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal mobility, gall bladder contraction, pancreatic enzyme secretion and are known to have a trophic action on the pancreas. They also inhibit gastric emptying and have various effects in the central nervous system.

Compounds which bind to cholecystokinin and/or gastrin receptors are important because of their potential pharmaceutical use as antagonists or partial agonists of the natural peptides.

A number of gastrin antagonists have been proposed for various therapeutic applications, including the prevention of gastrin-related disorders, gastrointestinal ulcers, Zollinger-Ellison syndrome, antral G cell hyperplasia and other conditions in which lower gastrin activity or lower acid secretion is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa and the treatment of pancreatic inflammation, biliary tract disease and various psychiatric disorders. Other possible uses are in the potentiation of opiate (for example morphine) analgesia and in the treatment of cancers, especially of the pancreas. Moreover, ligands for cholecystokinin receptors in the brain (so-called $CCK_2$ receptors) have been claimed to possess anxiolytic activity.

PCT/GB99/03733 describes a class of compounds having gastrin antagonist activity. This class of compounds is typically characterised by a 5-membered ring, preferably an imidazole or pyrrole, having two hydrocarbyl substituents and an amide or urea-type substituent.

According to the present invention, there are provided compounds of formula (I), (IIa) or (IIb).

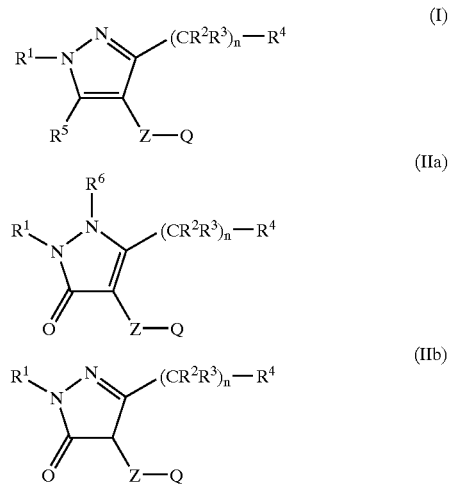

wherein n is from 1 to 4;

$R^1$ is H or $C_1$ to $C_{15}$ hydrocarbyl wherein up to three C atoms may optionally be replaced by N, O and/or S atoms and up to three H atoms may optionally be replaced by halogen atoms;

$R^2$ is selected from H, Me, Et, Pr and OH, each $R^2$ being independently selected from H, Me, Et, Pr and OH when n is greater than 1;

$R^3$ (when n is 1) is selected from H, Me, Et and Pr; or (when n is greater than 1) each $R^3$ is independently selected from H, Me, Et and Pr, or two $R^3$ groups on neighbouring carbon atoms are linked to form a $C_3$ to $C_6$ carbocyclic ring, or two $R^3$ groups are absent from neighbouring carbon atoms which are linked by a double bond; or $R^2$ and $R^3$ on the same carbon atom together represent an =O group;

$R^4$ is H or $C_1$ to $C_{15}$ hydrocarbyl wherein up to two C atoms may optionally be replaced by N, O and/or S atoms and up to three H atoms may optionally be replaced by halogen atoms;

$R^5$ is H, OH or $C_1$ to $C_{15}$ hydrocarbyl wherein up to two C atoms may optionally be replaced by N, O and/or S atoms and up to three H atoms may optionally be replaced by halogen atoms;

$R^6$ is H or $C_1$ to $C_{15}$ hydrocarbyl wherein up to two C atoms may optionally be replaced by N, O and/or S atoms and up to three H atoms may optionally be replaced by halogen atoms;

Z is —$(NR^7)_a$—CO—$(NR^8)_b$— (wherein a is 0 or 1, b is 0 or 1, and $R^7$ and $R^8$ are independently selected from H, Me, Et, Pr or Bn), —CO—$NR^7$—$CH_2$—CO—$NR^8$—, —CO—O—, —$CH_2$—$CH_2$—, —CH=CH—, —$CH_2$—$NR^8$— or a bond;

Q is —R⁹V, or

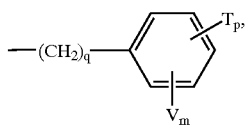

wherein R⁹ is —CH₂—; —CH₂—CH₂—; or

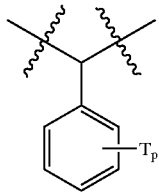

or R⁹ and R⁸, together with the nitrogen atom to which R⁸ is attached, form a piperidine or pyrrolidine ring which is substituted by V;

V is —CO—NH—SO₂-Ph, —SO₂—NH—CO-Ph, —CH₂OH, or a group of the formula —R¹⁰U, (wherein U is —COOH, tetrazolyl, —CONHOH— or —SO₃H; and R¹⁰ is a bond; $C_1$ to $C_6$ hydrocarbylene, optionally substituted by hydroxy, amino or acetamido; —O—($C_1$ to $C_3$ alkylene)-; —SO₂NR¹¹—CHR¹²—;

—CO—NR¹¹—CHR¹²—, R¹¹ and R¹² being independently selected from H and methyl; or —NH—(CO)$_c$—CH₂—, c being 0 or 1);

T is $C_1$ to $C_6$ hydrocarbyl, —NR⁷R⁸ (wherein R⁷ and R⁸ are as defined above), —OMe, —OH, —CH₂OH, halogen or trihalomethyl;

m is 1 or 2;

p is from 0 to 3; and q is from 0 to 2, with the proviso that q is 1 or 2 when Z is a bond);

or a pharmaceutically acceptable salt thereof.

In certain compounds according to the invention, Z is —(NR⁷)$_a$—CO—(NR⁸)$_b$—, —CO—NH—CH₂—CO—NH— or a bond; Q is

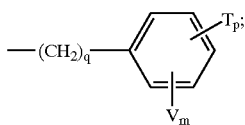

V is —CO—NH—SO₂-Ph, —SO₂—NH—CO-Ph, —OCH₂COOH, tetrazolyl or —(CH₂)$_s$COOH, wherein s is from 0 to 2; and T is $C_1$ to $C_6$ hydrocarbyl, —NR⁷R⁸, —OMe, —OH, —CH₂OH or halogen A further group of compounds according to the invention are those in Z is —(NR⁷)$_a$—CO—(NR⁸)$_b$—, Q is —(CH₂)$_r$COOH, wherein r is from 1 to 3; and T is $C_1$ to $C_6$ hydrocarbyl, —NR⁷R⁸, —OMe, —OH, —CH₂OH or halogen.

A still further group of compounds according to the invention are those in which -Z-Q is

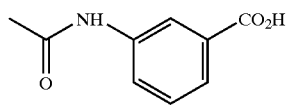

Preferably R¹ is $C_1$ to $C_{12}$ hydrocarbyl wherein one C atom may optionally be replaced by N or O and up to three H atoms may optionally be replaced by F, Cl or Br. More preferably R¹ is H; $C_3$ to $C_{12}$ alicyclic; phenyl, pyridyl, phenyl $C_1$–$C_3$ alkyl or pyridyl $C_1$–$C_3$ alkyl (all optionally substituted with OMe, NMe₂, CF₃, Me, F, Cl, Br or I); or $C_1$ to $C_8$ alkyl. Alicyclic groups include $C_5$ to $C_8$ cycloalkyl, $C_7$ to $C_{10}$ polycycloalkyl, $C_5$ to $C_8$ cycloalkenyl and $C_7$ to $C_{10}$ polycycloalkenyl, all optionally substituted with methyl. Phenyl $C_1$–$C_3$ alkyl includes, for example, benzyl.

Preferably R² is H, R³ is H and n is 1, 2 or 3.

In certain compounds according to this invention R⁴ is $C_3$ to $C_{15}$ carbocyclic, optionally substituted with 1, 2 or 3 halogen atoms. In other compounds according to this invention, R⁴ is —NH—R¹³ or —OR¹³, wherein R¹³ is $C_3$ to $C_{12}$ carbocyclic, optionally substituted with 1, 2 or 3 halogen atoms. Preferably R⁴ is —O-adamantyl, —O-cycloheptyl, —O-cyclohexyl or —O-phenyl. Most preferably R⁴ is —O-adamantyl.

Preferably R⁵ is H, OH or $C_1$ to $C_{12}$ hydrocarbyl wherein one C atom may optionally be replaced by N or O and up to three H atoms may optionally be replaced by F, Cl, or Br. More preferably R⁵ is H; OH; $C_3$ to $C_{12}$ alicyclic; O—$C_3$ to $C_{12}$ alicyclic; phenyl, pyridyl, phenyl $C_1$–$C_3$ alkyl, phenyl $C_1$–$C_3$ alkoxy, pyridyl $C_1$–$C_3$ alkyl, or pyridyl $C_1$–$C_3$ alkoxy (all optionally substituted with OMe, NMe₂, CF₃, Me, F, Cl, Br or I); $C_1$ to $C_8$ alkyl; or $C_1$ to $C_8$ alkoxy. Alicyclic groups include $C_5$ to $C_8$ cycloalkyl, $C_7$ to $C_{10}$ polycycloalkyl, $C_5$ to $C_8$ cycloalkenyl and $C_7$ to $C_{10}$ polycycloalkenyl, all optionally substituted with methyl. Phenyl $C_1$–$C_3$ alkyl includes, for example, benzyl.

Preferably R⁶ is H or $C_1$ to $C_{12}$ hydrocarbyl wherein one C atom may optionally be replaced by N or O and up to three H atoms may optionally be replaced by F, Cl, or Br. More preferably R⁶ is H; $C_3$ to $C_{12}$ alicyclic; phenyl, pyridyl, phenyl $C_1$–$C_3$ alkyl or pyridyl $C_1$–$C_3$ alkyl (all optionally substituted with OMe, NMe₂, CF₃, Me, F, Cl, Br or I); or $C_1$ to $C_8$ alkyl. Alicyclic groups include $C_5$ to $C_8$ cycloalkyl, $C_7$ to $C_{10}$ polycycloalkyl, $C_5$ to $C_8$ cycloalkenyl and $C_7$ to $C_{10}$ polycycloalkenyl, all optionally substituted with methyl. Phenyl $C_1$–$C_3$ alkyl includes, for example, benzyl.

Preferably Z is —CO—NH—.

Preferably Q is

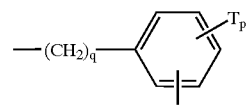

and more preferably

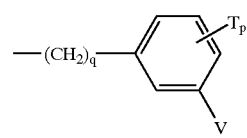

p is preferably 0 or 1, and q is preferably 0. If p is greater than 0, then T is preferably $C_1$ to $C_6$ hydrocarbyl or halo.

m is preferably 1, and V is preferably —$CO_2H$, —$CH_2CO_2H$ or tetrazolyl.

$R^{10}$ is preferably a bond, $C_1$ or $C_2$ alkylene (optionally substituted by hydroxy, amino or acetamido), —O—($C_1$ to $C_3$ alkylene)-; —$SO_2NR^{11}$—$CHR^{12}$—; —CO—$NR^{11}$—$CHR^{12}$—, —NH—(CO)$_c$—$CH_2$—, or a group of the formula

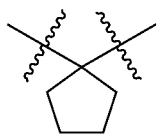

Certain compounds of the invention exist in various regioisomeric, enantiomeric, tautomeric and diastereomeric forms. It will be understood that the invention comprehends the different regioisomers, enantiomers, tautomers and diastereomers in isolations from each other as well as mixtures.

In particular, the skilled person will understand that the compound of formula (IIa) wherein $R^6$ is H and the compound of formula (IIb) are merely tautomers of the compound of formula (I) wherein $R^5$ is OH. These tautomers may exist in isolation from each other or as mixtures.

Compounds of present invention wherein
(i) $R^5$ is H
(ii) -Z-Q is

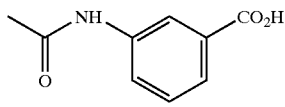

may be prepared by the route exemplified in Reaction Scheme 1.

β-Ketoester (III) is reacted with DMF dimethylacetal to yield α,β-unsaturated ketone (IV). Compound (IV) is treated with $R^1$—$NHNH_2$ to furnish the corresponding hydrazone which, in the presence of base (e.g. triethylamine), cyclises to form pyrazole (V). Conversion of the ester to an acid, followed by coupling (under acid activating conditions e.g via the acid chloride using oxalyl chloride) with an ester-substituted aniline and final unmasking of this ester furnishes the target carboxylic acid (VI). When, for example, the ester(s) are benzyl esters, the corresponding carboxylic acid(s) can be unmasked by catalytic hydrogenation. It will be readily apparent to the skilled person that other compounds of the present invention wherein $R^5$ is H can be prepared by appropriate manipulation of compound (V).

Compounds of the present invention wherein (i) $R^5$ is $C_3$ to $C_{12}$ alicyclic; phenyl (optionally substituted with OMe, $NMe_2$, $CF_3$, Me, F, Cl, Br, I or OH); or $C_1$ to $C_8$ alkyl (ii) -Z-Q is

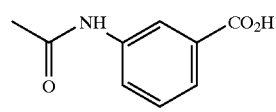

may be prepared by the route exemplified in Reaction Scheme 2.

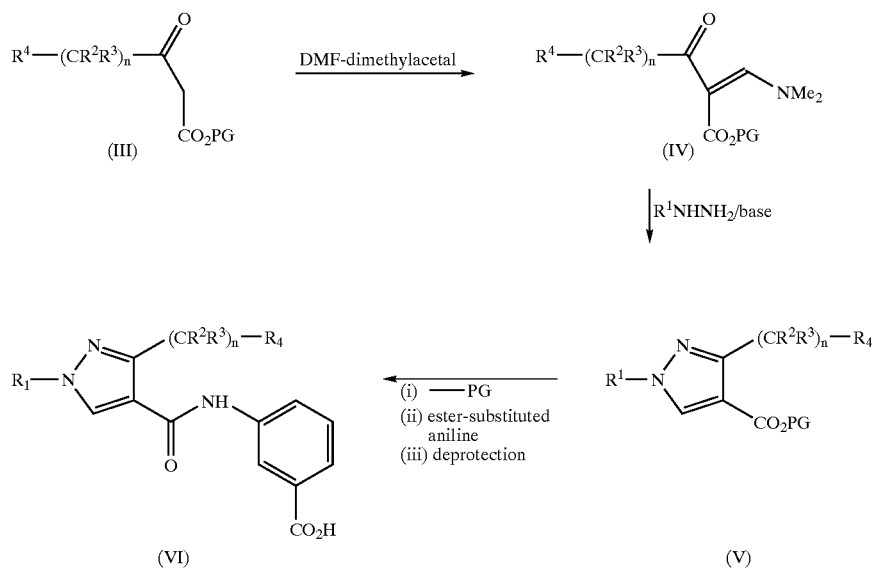

Reaction Scheme 2

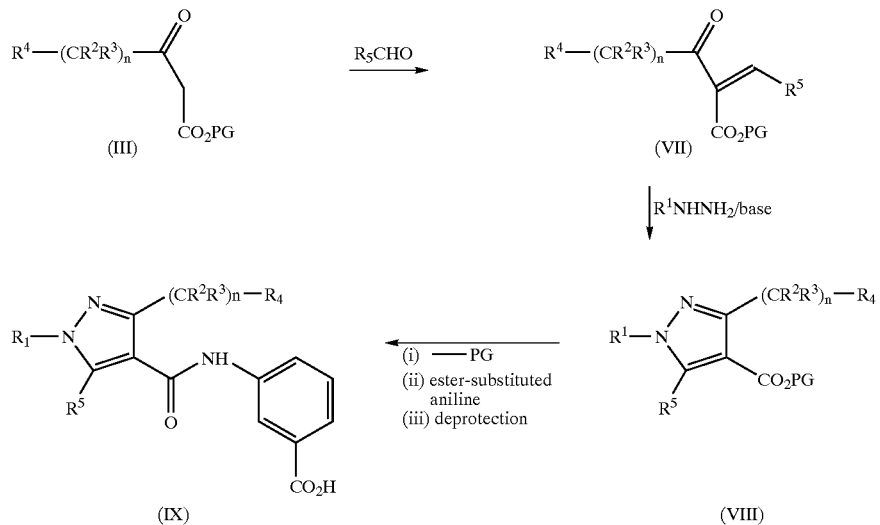

β-Ketoester (III) is reacted with $R^5$—CHO/ ethylenediamine diacetate to yield α,β-unsaturated ketone (VII). Treatment of ketone (VII) with $R^1$—$NHNH_2$ affords a hydrazone which, in the presence of base (e.g. DBU), cyclises to furnish pyrazole (VIII). Pyrazole (VIII) is converted to the target carboxylic acid (IX) by the same route shown and described in Reaction Scheme 1. It will be readily apparent to the skilled person that other compounds of the present invention wherein $R^5$ is $C_3$ to $C_{12}$ alicyclic; phenyl (optionally substituted with OMe, $NMe_2$, $CF_3$, Me, F, Cl, Br, I or OH); or $C_1$ to $C_8$ alkyl can be prepared by appropriate manipulation of compound (VIII).

Compounds of the present invention wherein (i) $R^5$ is OH (ii) -Z-Q is

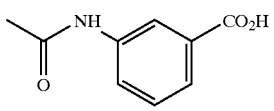

may be prepared by the route exemplified in Reaction Scheme 3.

Reaction Scheme 3

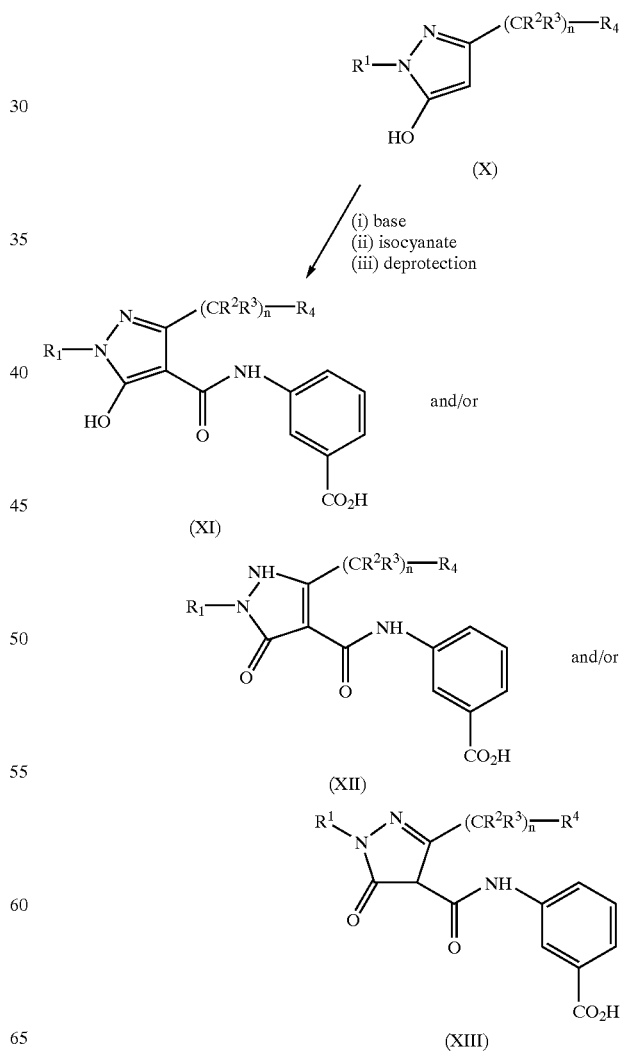

β-Ketoester (III) is reacted with $R^1$—$NHNH_2$ to form a hydrazone which, in the presence of base (e.g. DBU), cyclises to form hydroxy-substituted pyrazole (X). Deprotonation of pyrazole (X) with for example NaH, followed by treatment of the resultant anion with an appropriate isocyanate (e.g. ethylcarbonylphenylisocyanate) affords an amide. Final deprotection of the ester group furnishes the requisite hydroxy-substituted pyrazole (XI) and/or its tautomers (XII) and (XIII). The ratio of (XI):(XII):(XIII) will vary from 100:0:0 to 0:100:0 to 0:0:100, depending on the other substituents present on the pyrazole ring. It will be readily apparent to the skilled person that other compounds of the present invention wherein $R^5$ is OH can be prepared by appropriate manipulation of compound (X).

Still referring to Reaction Scheme 3, compounds of the present invention wherein $R^5$ is OMe may be prepared by alkylation of (XI) with dimethyl sulfate. It may also be prepared by alkylation of a protected precursor of (XI), with, for example, dimethyl sulfate as shown in Reaction Scheme 4.

Still referring to Reaction Scheme 3, compounds of the present invention wherein $R^6$ is Me may be prepared by alkylation of (XII) with dimethyl sulfate. It may also be prepared by alkylation of a protected precursor of (XII), with, for example, methyl iodide as shown in Reaction Scheme 5.

Compounds of the present invention wherein (i) $R^5$ is OMe (ii) -Z-Q is

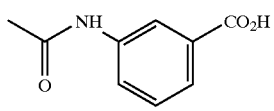

may be prepared by the route exemplified in Reaction Scheme 4.

Reaction Scheme 4

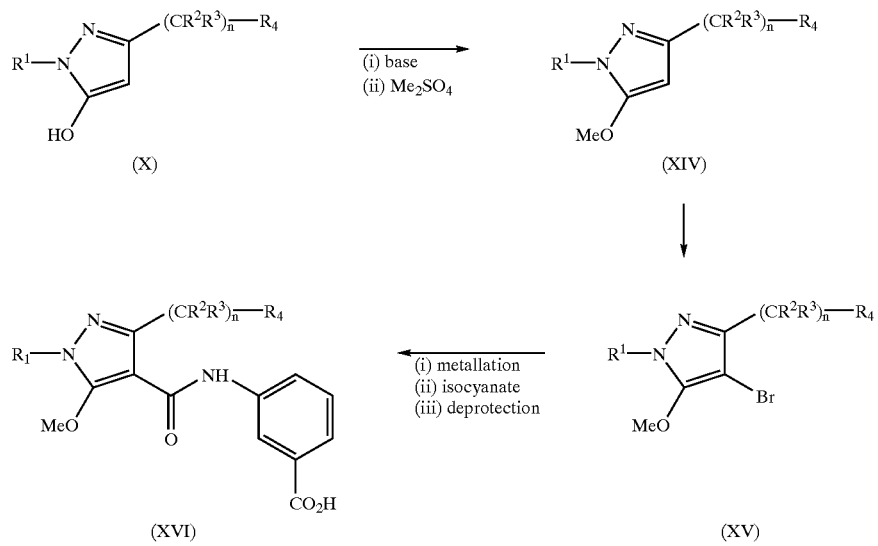

Hydroxypyrazole (X) is treated with base then dimethyl sulfate to afford methoxypyrazole (XIV). Bromination with, for example, NBS gives the bromo-substituted pyrazole (XV). Finally, metallation, reaction with an appropriate isocyanate (e.g. ethylcarbonylphenylisocyanate) and deprotection furnishes the requisite methoxy-substituted pyrazole compound (XVI).

Compounds of the present invention wherein (i) $R^6$ is Me (ii) -Z-Q is

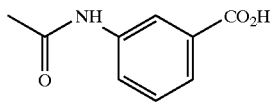

may be prepared by the route exemplified in Reaction Scheme 5.

Reaction Scheme 5

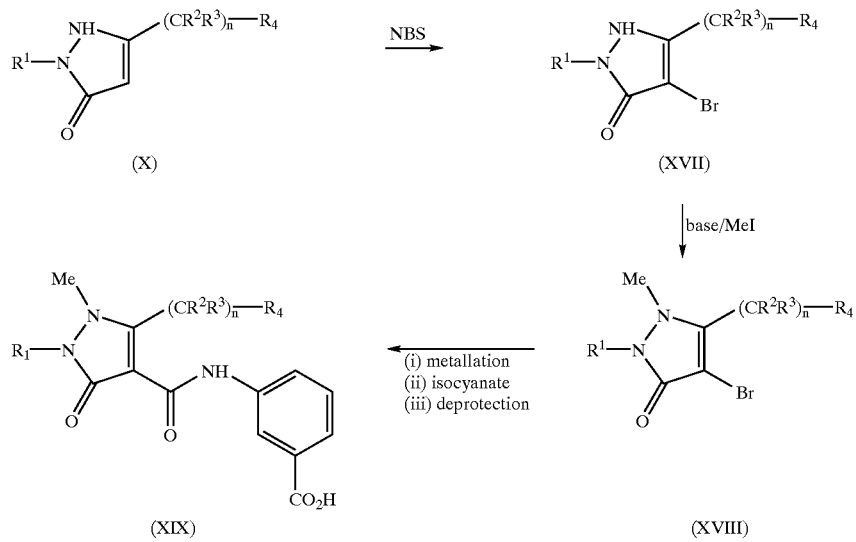

Bromination of hydroxypyrazole (X) followed by alkylation of the pyrazole nitrogen affords (XVIII). Metallation, reaction with isocyanate and deprotection as described previously furnishes the requisite pyrazole compound (XIX).

Hence, the present invention provides methods of making compounds according to formulae (I), (IIa) or (IIb).

The invention also comprehends derivative compounds ("pro-drugs") which are degraded in vivo to yield the species of formula (I) or (II). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, 1985, pp. 112–176, and *Drugs*, 1985, 29, pp. 455–473.

Pro-drug forms of the pharmacologically-active compounds of the invention will generally be compounds according to formula (I) or (II) having an acid group which is esterified or amidated. Included in such esterified acid groups are groups of the form —COOR$^a$, wherein R$^a$ is C$_1$ to C$_5$ alkyl, phenyl, substituted phenyl, benzyl, substituted benzyl, or one of the following:

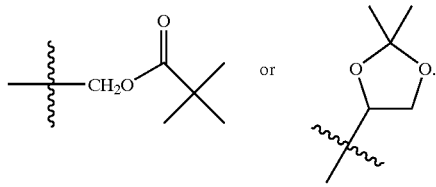

Amidated acid groups include groups of the formula —CONR$^b$R$^c$, wherein R$^b$ is H, C$_1$ to C$_5$ alkyl, phenyl, substituted phenyl, benzyl, or substituted benzyl, and R$^c$ is —OH or one of the groups just recited for R$^b$.

Compounds of formula (I) or (II) having an amino group may be derivatised with a ketone or an aldehyde such as formaldehyde to form a Mannich base. This will hydrolyse with first order kinetics in aqueous solution.

Another aspect of the present invention is a pharmaceutical composition comprising a compound of formula (I) or (II) substantially as described herein before with a pharmaceutically acceptable diluent or carrier.

Yet another aspect of the present invention is a method of making a pharmaceutical composition comprising a compound of formula (I) or (II) substantially as described herein before, comprising mixing said compound with a pharmaceutically acceptable diluent or carrier.

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained be conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 $\mu$g/kg and 50 mg/kg, especially between 10 $\mu$g/kg and 10 mg/kg, eg. between 100 $\mu$g/kg and 2 mg/kg.

In a further aspect of the present invention there are provided pharmaceutical compositions comprising a compound according to formula (I) or (II) and a proton pump inhibitor. Compositions comprising a CCK/gastrin antagonist and a proton pump inhibitor are described in International patent application WO93/12817, incorporated herein by reference.

In one aspect of the present invention the proton pump inhibitor is
omeprazole which is 5-methoxy-2-[[(4-methoxy-3,5-dimethyl-2-pyridinyl)methyl]sulfinyl]-1H-benzimidazole;
BY308;
SK & 95601 which is 2-[[(3-chloro-4-morpholino-2-pyridyl)methyl]sulfinyl]-5-methoxy-(1H)-benzimidazole;
SK & 96067 which is 3-butyryl-4-(2-methylphenylamino)-8-methoxyquinoline;
5-trifluoromethyl-2-[4-methoxy-3-methyl-2-pyridyl-methyl]-thio-[1H]-benzimidazole;
or pharmaceutically acceptable salts thereof.

These proton pump inhibitors are described and claimed in U.S. Pat. Nos. 4,472,409 and 4,255,431. These patents are incorporated herein by reference.

In a further aspect of the present invention, the proton pump inhibitor is
lansoprazole which is 2-[[[3-methyl-4-(2,2,2-trifluoroethoxy)-2-pyridinyl]methyl]sulfinyl]-1H-benzimidazole;
pantoprazole which is 5-(difluoromethoxy)-2-[[(3,4-dimethoxy-2-pyridinyl)methyl]sulfinyl]-1H-benzimidazole;
perprazole;
rabeprazole which is 2-[[4-(3-methoxypropoxy)-3-methylpyridin-2-yl]methylsulfinyl]-1H-benzimidazole;
[[4-(2,2,2-trifluoroethoxy)-3-methyl-2-pyridyl]-methyl] sulfenamide;
(Z)-5-methyl-2-[2-(1-naphthyl)ethenyl]-4-piperidinopyridine HCl;
2-(4-cyclohexyloxy-5-methylpyridin-2-yl)-3-(1-naphthyl)-1-propanol;
methyl 2-cyano-3-(ethylthio)-3-(methylthio)-2propenoate;
2-((4-methoxy-2-pyridyl)methylsulphinyl)-5-(1,1,2,2-tetrafluoroethoxy)-1H-benzimidazole sodium;
2-[[[4-(2,2,3,3,4,4,4-heptafluorobutoxy)-2-pyridyl]methyl) sulfinyl]-1H-thieno[3,4-d]imidazole;
2-[[[4-(2,2,2-trifluoroethoxy)-3-methyl-2-pyridyl]methyl] sulfinyl]-1H-benzimidazole;
2-[[[4-(2,2,2-trifluoroethoxy)-3-methyl-2-pyridyl]methyl] sulfinyl]-1H-benzimidazole;
2-methyl-8-(phenylmethoxy)-imidazo(1,2-A)-pyridine-3-acetonitrile;
(2-((2-dimethylaminobenzyl)sulfinyl)-benzimidazole);
4-(N-allyl-N-methylamino)-1-ethyl-8-((5-fluoro-6-methoxy-2-benzimidazolyl)sulfinylmethyl)-1-ethyl 1,2,3, 4-tetrahydroquinolone;
2-[[(2-dimethylaminophenyl)methyl]sulfinyl]-4,7-dimethoxy-1H-benzimidazole;
2-[(2-(2-pyridyl)phenyl)sulfinyl)-1H-benzimidazole;
(2-[(2-amino-4-methylbenzyl)sulfinyl]-5-methoxybenzo[d] imidazole;
(4(2-methylpyrrol-3-yl)-2-guanidisothiazole);
4-(4-(3-(imidazole)propoxy)phenyl)-2phenylthiazole;
(E)-2-(2-(4-(3-(dipropylamino)butoxy)phenyl)-ethenyl) benzoxazole;
(E)-2-(2-(4-(3-(dipropylamino)propoxy)phenyl)ethenyl)-benzothiazole;
Benzeneamine, 2-[[(5-methoxy-1H-benzimidazol-2-yl) sulfinyl]methyl)-4-methyl-;
Pumilacidin A;
2,3-dihydro-2-methoxycarbonylamino-1,2-benzisothiazol-3-one;
2-(2-ethylaminophenylmethylsulfinyl)-5,6-dimethoxybenzimidazole;
2-methyl-8-(phenylmethoxy)imidazo[1,2-a)pyridine-3-acetonitrile;
3-amino-2-methyl-8-phenylmethoxyimidazo[1,2-a)-pyrazine HCl;
2-[[(3-chloro-4-morpholino-2-pyridyl)methyl]-sulfinyl)-5-methoxy-(1H)-benzinidazole;
[3-butyryl-4-(2-methylphenylamino)-8-methoxy-quinoline);
2-indanyl 2-(2-pyridyl)-2-thiocarbamoylacetate HCl;
2,3-dihydro-2-(2-pyridinyl)-thiazolo (3,2-a)-benzimidazole;
3-cyanomethyl-2-methyl-8-(3-methyl-2-butenyloxy)-(1,2-a)imidazopyridine;
zinc L-carnosine;
or pharmaceutically acceptable salts thereof.

Rabeprazole is described in U.S. Pat. No. 5,045,552. Lansoprazole is described in U.S. Pat. No. 4,628,098. Pantoprazole is described in U.S. Pat. No. 4,758,579. These patents are incorporated herein by reference.

Preferably, the proton pump inhibitor is selected from (RS)-rabeprazole, (RS)-omeprazole, lansoprazole, pantoprazole, (R)-omeprazole, (S)-omeprazole, perprazole, (R)-rabeprazole, (S)-rabeprazole, or the alkaline salts thereof. The alkaline salts may be, for example, the lithium, sodium, potassium, calcium or magnesium salts.

Compositions of this invention comprising a compound of formula (I) or (II) and a proton pump inhibitor may be administered as described above. Preferably the dose of each of the active ingredients in these compositions will be equal to or less than that which is approved or indicated in monotherapy with said active ingredient.

In another aspect of this invention, there is provided a kit comprising a compound of formula (I) or (II) and a proton pump inhibitor. The kit is useful as a combined preparation for simultaneous, separate or sequential use in the treatment of patients suffering from gastrointestinal disorders.

In yet a further aspect of the present invention there is provided a method of making a pharmaceutical composition comprising a compound of formula (I) or (II) substantially as described herein before and a proton pump inhibitor, comprising mixing said compound and said proton pump inhibitor with a pharmaceutically acceptable carrier or diluent.

The term "hydrocarbyl" is used herein to refer to monovalent groups consisting of carbon and hydrogen. Hydrocarbyl groups thus include alkyl, alkenyl and alkynyl groups (in both straight and branched chain forms), cycloalkyl (including polycycloalkyl), cycloalkenyl and aryl groups, and combinations of the foregoing, such as alkylcycloalkyl, alkylpolycycloalkyl, alkylaryl, alkenylaryl, alkynylaryl, cycloalkylaryl and cycloalkenylaryl groups.

Where reference is made to a carbon atom of a hydrocarbyl group being replaced by a N, O or S atom, what is intended is that

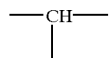

is replaced by

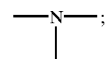

or that —CH$_2$— is replaced by —O— or —S—.

A "carbocyclic" group, as the term is used herein, comprises one or more closed chains or rings, which consist entirely of carbon atoms. Carbocyclic groups thus include aryl groups (such as phenyl, naphthyl, indanyl, fluorenyl, (1,2,3,4)-tetrahydronaphthyl, indenyl and isoindenyl, and substituted derivatives thereof), and also alicyclic groups. The term "alicyclic group" refers to a carbocyclic group which does not contain an aromatic ring, and thus includes groups such as cyclopropyl, cyclobutyl, cyclopentyl, cyclohexyl, cyclohexenyl, adamantyl, norbornyl, bicyclo [2.2.2]octyl, norbornenyl and bicyclo[2.2.2]octenyl, and also groups (such as adamantanemethyl and methylcyclohexyl) which contain both alkyl or alkenyl groups in addition to cycloalkyl or cycloalkenyl moieties.

The term "aryl" is used herein to refer to an aromatic group, such as phenyl or naphthyl, or a heteroaromatic group, such as pyridyl, pyrrolyl, or furanyl.

The term "alkyl" is used herein to refer to both straight and branched chain forms.

When reference is made herein to a substituted carbocyclic group (such as substituted phenyl) or a substituted heterocyclic group, the substituents are preferably from 1 to 3 in number and selected from $C_1$ to $C_6$ alkyl, $C_1$ to $C_6$ alkoxy, thio, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy ($C_1$ to $C_6$)alkyl, di($C_1$ to $C_6$ alkyl)aminocarboxy($C_1$ to $C_6$)alkyl, $C_1$ to $C_6$ alkylcarbonylamino, $C_5$ to $C_8$ cycloalkyl, $C_5$ to $C_8$ cycloalkyl($C_1$ to $C_6$)alkyl, $C_1$ to $C_6$ alkylcarbonyl ($C_1$ to $C_6$ alkyl)amino, aryl, aryl($C_1$ to $C_6$)alkyl, ($C_1$ to $C_6$ alkyl)aryl, halo, $C_1$ to $C_6$ alkylhalo, sulphamoyl, tetrazolyl and cyano.

Most usually, substituents will be selected from $C_1$ to $C_6$ alkyl, $C_1$ to $C_6$ alkoxy, thio, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy ($C_1$ to $C_6$)alkyl, di($C_1$ to $C_6$ alkyl)aminocarboxy($C_1$ to $C_6$)alkyl, $C_1$ to $C_6$ alkylcarbonylamino, $C_5$ to $C_8$ cycloalkyl, $C_5$ to $C_8$ cycloalkyl($C_1$ to $C_6$)alkyl, $C_1$ to $C_6$ alkylcarbonyl ($C_1$ to $C_6$ alkyl)amino, halo, $C_1$ to $C_6$ alkylhalo, sulphamoyl, tetrazolyl and cyano.

The term "halogen" is used herein to refer to any of fluorine, chlorine, bromine and iodine. Most usually, however, halogen substituents in the compounds of the invention are chlorine and fluorine substituents.

The term "suitably protected" used herein refers to the use of any suitable protecting group to protect a functional group. Such protecting groups are denoted as PG, PG$^1$, PG$^2$, PG$^3$ etc. as shown in the Reaction Schemes above. Suitable protecting groups will be readily apparent to the skilled person and may be found in, for example, Kocienski, *Protecting Groups*, Thieme, New York, 1994. For example, in the case of hydroxyl groups, suitable protecting groups may include esters, ethers (e.g. silyl ethers or alkyl ethers) or acetals. Some specific examples of typical hydroxyl protecting groups are allyl, Aloc, benzyl, BOM, t-butyl, trityl, TBS, TBDPS, TES, TMS, TIPS, PMB, MEM, MOM, MTM, and THP. In the case of nitrogen atoms, suitable protecting groups may include Boc, Aloc, Troc, benzyl, allyl, Fmoc or silyl. In the case of carboxylic acids, suitable protecting groups may include esters (e.g. benzyl, allyl, methyl or ethyl esters).

The term "activated" used herein in connection with carboxylic acids refers to any activated derivative of a carboxylic acid. Methods of activating carboxylic acids will be known to the skilled artisan and may include activation using EDC, CDI or DCC (optionally in the presence of nucleophilic catalysts such as DMAP), conversion to an acid halide such as an acid chloride (e.g. using SOCl$_2$ or oxalyl chloride) or conversion to an activated ester (such as a phenyl or pentafluorophenyl ester).

The invention is now further illustrated by means of the following Examples. All reactions were performed under an atmosphere of dry argon unless otherwise stated. Dichloromethane (DCM) was freshly distilled from calcium hydride. Anhydrous tetrahydrofuran (THF) and N,N-dimethylformamide (DMF) were used.

EXAMPLE 1

Reaction Scheme 1

Step a. 2-[2-(Adamantan-1-yloxy)-acetyl]-3-dimethylamino-acrylic acid benzyl ester.

A solution of 4-(adamantan-1-yloxy)-3-oxo-butyric acid benzyl ester (1.133 g, 3.3 mmol) and DMF dimethylacetal (0.56 mL, 3.96 mmol) in DMF (20 mL) was heated at 100° C. for 3 h. The mixture was diluted with $H_2O$ (80 mL) and extracted with EtOAc (2×30 mL). The combined extracts were washed with brine (2×30 mL), and dried ($MgSO_4$). Filtration and evaporation of the solvent afforded the product, (0.647 g, 49%).

$^1$H NMR. ($CDCl_3$) δ 7.67 (1H, s), 7.43–7.27 (5H, m), 5.20 (2H, s), 4.34 (2H, s), 3.07–2.89 (6H, b.m), 2.10 (3H, br.s), 1.70 (6H, s), 1.58 (6H, s).

Step b. 3-(Adamantan-1-yloxymethyl)-1-o-tolyl-1H-pyrazole-4-carboxylic acid benzyl ester.

$NEt_3$ (0.2 mL, 1.43 mmol) was added to a mixture of 2-[2-(adamantan-1-yloxy)-acetyl]-3-dimethylamino-acrylic acid benzyl ester (0.539 g, 1.4 mmol), and o-tolylhydrazine hydrochloride (0.222 g, 1.4 mmol) in MeCN (8 mL) at 0° C. The mixture was allowed to warm to room temperature and stirred for 17 h. The precipitated solid was filtered off, washed with MeCN and dried to afford the product, (0.359 g, 56%).

$^1$H NMR. ($CDCl_3$) δ 8.10 (1H, s) 7.48–7.27 (9H, m), 5.33 (2H, s), 4.55 (2H, s) 2.07 (3H, s), 2.02 (3H, br.s), 1.58–1.43 (12H, m).

Step c. 3-(Adamantan-1-yloxymethyl)-1-o-tolyl-1H-pyrazole-4-carboxylic acid.

A solution of 3-(adamantan-1-yloxymethyl)-1-o-tolyl-1H-pyrazole-4-carboxylic acid benzyl ester (0.359 g, 0.79 mmol) in MeOH-THF (1:1/24 mL) was hydrogenated over 10% palladium on charcoal (50 mg) for 19 h. The reaction mixture was filtered through a pad of Celite and the filtrate evaporated to afford the product, (0.29 g, 100%).

$^1$H NMR (DMSO-$d_6$) δ 7.97 (1H, s), 7.46–7.30 (4H, m), 4.53 (2H, s), 1.96 (6H, s), 1.52–1.36 (12H, m).

Step d. 3-{[3-(Adamantan-1-yloxymethyl)-1-o-tolyl-1H-pyrazole-4-carbonyl]-amino}-benzoic acid benzyl ester.

Oxalyl chloride (100 μl, 1.15 mmol) was added to a solution of 3-(adamantan-1-yloxymethyl)-1-o-tolyl-1H-pyrazole-4-carboxylic acid (248 mg, 0.56 mmol) and DMF (5 drops) in $CH_2Cl_2$ (7.5 mL). The reaction mixture was stirred until evolution of carbon dioxide ceased then the solution was evaporated in vacuo. The acid chloride obtained was dissolved in THF (5 mL) and added dropwise to a solution of 3-amino-benzoic benzyl ester (146 mg, 0.64 mmol) and i-$PrNEt_2$ (120 μl, 0.69 mmol) in THF (12 mL) and stirred at room temperature for 16 h. The solution was diluted with EtOAc (20 mL) washed with 1N HCl (20 mL), saturated $NaHCO_3$ solution (20 mL), brine (20 mL), and dried ($MgSO_4$). Filtration and evaporation afforded the product as a red oil (450 mg, 100%).

$^1$H NMR ($CDCl_3$) δ 9.78 (1H, s), 8.20 (1H, s), 8.15 (1H, d), 8.10 (1H, s), 7.80 (1H, d), 7.47–7.29 (9H, m), 5.38 (2H, s), 4.36 (2H, s), 2.09 (6H, 2×s), 1.68 (6H, s), 1.58 (6H, m).

Step e. 3-{[3-(Adamantan-1-yloxymnethyl)-1-o-tolyl-1H-pyrazole-4-carbonyl]-amino}-benzoic acid.

A solution of 3-{[3-(adamantan-1-yloxymethyl)-1-o-tolyl-1H-pyrazole-4-carbonyl]-amino}-benzoic acid benzyl ester (450 mg, 0.8 mmol) in MeOH-THF (10:1/22 mL) was hydrogenated over 10% palladium on charcoal (69 mg) for 20 h. The reaction mixture was filtered through a pad of Celite and the filtrate evaporated. The residue was purified by flash column chromatography on silica gel by elution with $CH_2Cl_2$/MeOH/acetic acid (9:1:0.1) to afford the product, (290 mg, 75%).

$^1$H NMR (DMSO-$d_6$) δ 10.08 (1H, s), 8.33 (1H, s), 8.32 (1H, s), 8.00 (1H, d), 7.66 (1H, d), 7.49–7.33 (5H, m), 4.61 (2H, s), 1.99 (3H, s), 1.96 (3H, s), 1.52–1.38 (12H, m).

The compound was further characterised as the N-methyl-D-glucamine salt. Found: C, 60.51; H, 7.51; N, 7.75%; $C_{36}H_{48}N_4O_9·2H_2O$ Requires: C, 60.32; H, 7.31; N, 7.82%.

EXAMPLE 2

Reaction Scheme 2

Step a. 2-[2-(Adamantan-1-yloxy)-3-acetyl]-3-phenyl-acrylic acid benzyl ester.

A solution of 4-(adamantan-1-yloxy)-3-oxo-butyric acid benzyl ester (1.138 g, 3.3 mmol), benzaldehyde (0.67 mL, 6.6 mmol) and ethylenediamine diacetate (124 mg, 0.69 mmol) in DMF (15 mL) was stirred at room temperature for 3 h. Pyridine (3 mL) was added and the mixture heated at 70° C. for 17 h. The reaction mixture was diluted with 5% $KHSO_4$ (50 mL) and extracted with EtOAc (2×40 mL). The combined extracts were washed with brine (50 mL), and dried ($MgSO_4$). Filtration and evaporation of the solvent gave the crude product which was a mixture of E and Z isomers and which was purified by flash column chromatography on silica gel, by elution with $CH_2Cl_2$/EtOAc (50:1), (729 mg, 51%).

$^1$H NMR ($CDCl_3$) δ (E-isomer) 7.80 (1H, s), 7.43–7.33 (10H, m) 5.28 (2H, s), 4.20 (2H, s), 2.06 (3H, br.s), 1.60–1.48 (12H, m): δ (Z-isomer) 7.80 (1H, s), 7.39–7.27 (10H, m), 5.28 (2H, s), 4.34 (2H, s), 2.14 (3H, br.s), 1.73–1.52 (12H, m).

Step b. 3-(Adamantan-1-yloxymethyl)-3-phenyl-1-o-tolyl-1H-pyrazole-4-carboxylic acid benzyl ester.

A solution of a mixture of E- and Z- isomers of 2-[2-(adamantan-1-yloxy)-3-acetyl]-3-phenyl-acrylic acid benzyl ester (645 mg, 1.5 mmol), i-$PrNEt_2$ (280 μl, 1.6 mmol), o-tolylhydrazine hydrochloride (236 mg, 1.5 mmol) and 1,8-diazabicyclo[5.4.0]undec-7-ene (225 μL, 1.5 mmol) in DMF (8 mL) was heated at 70° C. for 16 h. The mixture was partitioned between 5% $KHSO_4$ (60 mL) and EtOAc (60 mL). The organic phase was separated, washed with brine (2×60 mL) and dried ($MgSO_4$). Filtration and evaporation gave the crude product which was purified by flash column chromatography, by elution with $CH_2Cl_2$/EtOAc (40:1). The product was obtained as a yellow oil, (371 mg, 46%).

$^1$H NMR ($CDCl_3$) δ 7.65 (2H, m), 7.39–7.26 (12H, m), 5.26 (2H, s), 4.54 (2H, s), 2.16 (3H, s), 2.02 (3H, br.s), 1.59–1.43 (12H, m).

Step c. 3-{[3-(Adamantan-1-yloxymethyl)-3-phenyl-1-o-tolyl-1H-pyrazole-4-carbonyl]-amino}-benzoic acid.

The title compound was prepared by the same method used to prepare example 1, except that 3-(adamantan-1-yloxymethyl)-3-phenyl-1-o-tolyl-1H-pyrazole-4-carboxylic acid benzyl ester was used in step c in place of 3-(adamantan-1-yloxymethyl)-1-o-tolyl-1H-pyrazole-4-carboxylic acid benzyl ester.

$^1$H NMR (DMSO-$d_6$) δ 12.87 (1H, br.s), 10.29 (1H, s), 8.28 (1H, s), 7.84 (1H, d), 7.68 (1H, 3H, m), 7.47–7.33 (8H, m), 4.38 (2H, s), 3.12 (3H, s), 1.93 (3H, br.s), 1.50–1.36 (12H, m).

The compound was further characterised as the N-methyl-D-glucamine salt. Found: C, 60.47; H, 7.15; N, 6.95%; $C_{42}H_{52}N_4O_9·1.5H_2O$ Requires: C, 64.35; H, 7.07; N, 7.15%.

EXAMPLE 3

Reaction Scheme 3

Step a. 5-(Adamantan-1-yloxymethyl)-2-o-tolyl-2H-pyrazol-3-ol

A mixture of 4-(adamantan-1-yloxy)-3-oxo-butyric acid benzyl ester (334 mg, 0.98 mmol), o-tolyl hydrazine hydrochloride (163 mg, 1.0 mmol), and $NEt_3$ (140 μL, 1.0 mmol) in EtOH (6 mL) was stirred at room temperature for 1 hr. The mixture was evaporated and the residue partitioned between EtOAc (40 mL) and H$_2$O (40 mL). The organic phase was separated, washed with brine (20 mL), and dried (MgSO$_4$). Filtration and evaporation of the solvent gave the crude hydrazone. 1,8-Diazabicyclo[5.4.0]undec-7-ene (150 µl, 1.0 mmol) was added to a solution of the hydrazone in DMF (4 mL), and the solution stirred at room temperature for 17 h. The mixture was partitioned between 5% KHSO$_4$ (60 mL) and EtOAc (60 mL). The organic layer was washed with brine (2×30 mL), and dried (MgSO$_4$). Filtration and evaporation of the solvent gave the product as a solid which was triturated with ether, isolated by filtration and dried (170 mg, 51%).

$^1$H NMR (DMSO-d$_6$) δ 10.44 (1H, s), 7.30 (4H, m), 5.40 (1H, s), 4.27 (2H, s), 2.10 (6H, 2×s), 1.74 (6H, s), 1.58 (6H, s).

Step b. 3-{[3-(Adamantan-1-yloxymethyl)-5-hydroxy-1-o-tolyl-1H-pyrazole-4-carbonyl]-amino}-benzoic acid ethyl ester.

A solution of 5-(adamantan-1-yloxymethyl)-2-o-tolyl-2H-pyrazol-3-ol (160 mg, 0.47 mmol) in anhydrous THF (4 mL) was added to a suspension of sodium hydride (26 mg of 60% dispersion in oil, 0.65 mmol) in THF (2 mL) under a dry argon atmosphere at room temperature. The mixture was stirred for 30 min. and a solution of 3-ethoxycarbonylphenyl isocyanate (99 mg, 0.5 mmol) in THF (1 mL) added. Stirring was continued for 1 h and the mixture partitioned between 5% KHSO$_4$ (40 mL) and EtOAc (40 mL). The organic phase was washed with brine (30 mL), and dried (MgSO$_4$). Filtration and evaporation of the solvent afforded the product as a red solid, (250 mg, 100%).

$^1$H NMR (CDCl$_3$) δ 10.45 (1H, s), 8.16 (1H, s), 8.03 (1H, d), 7.83 (1H, d), 7.44 (1H, t), 7.28 (4H, m), 4.81 (2H, s), 4.38 (2H, q), 2.22 (3H, s), 2.15 (3H, s), 1.94 (6H, s), 1.65 (6H, s) 1.40 (3H, t).

Step c. 3-{[3-(Adamantan-1-yloxymethyl)-5-hydroxy-1-o-tolyl-1H-pyrazole-4-carbonyl]-amino}-benzoic acid.

A solution of 3-{[3-(adamantan-1-yloxymethyl)-5-hydroxy-1-o-tolyl-1H-pyrazole-4-carbonyl]-amino}-benzoic acid ethyl ester (249 mg, 0.47 mmol) and potassium hydroxide (208 mg, 3.7 mmol) in EtOH—H$_2$O (4:1/15 mL) was refluxed for 1 h. On cooling to room temperature the solution was acidified with 5% KHSO$_4$. The precipitated solid was filtered off, washed with H$_2$O and dried to afford the product, (201 mg, 85%).

$^1$NMR (DMSO-d$_6$) δ 13.30 (1H, br.s), 12.90 (1H, s), 10.77 (1H, s), 8.28 (1H, s), 7.72 (1H, d), 7.60 (1H, d), 7.45–7.31 (5H, m), 4.91 (2H, s), 2.19 (3H, s) 2.12 (3H, br.s), 1.80 (6H, s), 1.57 (6H, s).

The compound was further characterised as the N-methyl-D-glucamine salt. Found: C, 59.19; H, 7.29; N, 7.51%; C$_{36}$H$_{48}$N$_4$O$_{10}$·2 H$_2$O Requires: C. 59.00; H, 7.15; N, 7.65%.

EXAMPLE 4

Reaction Scheme 3

Step a. 5-(Adamantan-1-yloxymethyl)-2-cyclohexyl-2H-pyrazol-3-ol

NEt$_3$ (800 µl, 5.7 mmol) was added to a solution of 4-(adamantan-1-yloxy)-3-oxo-butyric acid benzyl ester (1.91 g, 5.6 mmol), and cyclohexyl hydrazine hydrochloride (877 mg, 5.82 mmol) in EtOH (30 mL) at 0° C. The mixture was allowed to warm to room temperature and stirred for 4 h. The precipitated white solid was filtered and dried to afford the product as a white solid, (1.23 g, 66%.).

$^1$H NMR (DMSO-d$_6$) δ 5.31 (1H, s), 4.24 (2H, s), 4.01 (1H, m), 2.18 (3H, br.s), 1.85–1.58 (19H, m), 1.40–1.20 (3H m).

Step b. 3-{[3-(Adamantan-1-yloxymethyl)-1-cyclohexyl-5-hydroxyl-1H-pyrazole-4-carbonyl]-amino}-benzoic acid.

The compound was prepared by the same procedure used in the preparation of Example 3, except that 5-(adamantan-1-yloxymethyl)-2-cyclohexyl-2H-pyrazol-3-ol was used in step b in place of 5-(adamantan-1-yloxymethyl)-2-o-tolyl-2H-pyrazol-3-ol.

$^1$H NMR (CDCl$_3$) δ 10.75 (1H, br.s), 10.34 (1H, s), 8.25 (1H, s), 7.98 (1H, d), 7.86 (1H, d), 7.47 (1H, t), 4.73 (2H, s), 4.12 (1H, m), 2.20 (1H, br. s), 1.92 (13H, m), 1.66 (6H, m), 1.43–1.19 (3H, m).

The compound was further characterised as the N-methyl-D-glucamine salt. Found: C, 58.12; H, 7.87; N, 7.58%; C$_{35}$H$_{52}$N$_4$O$_{10}$·2 H$_2$O Requires: C, 58.00; H, 7.79; N, 7.73%.

EXAMPLE 5

Reaction Scheme 4

Step a. 3-(Adamantan-1-yloxymethyl)-1-cyclohexyl-5-methoxy-1H-pyrazole 5-(Adamantan-1-yloxymethyl)-2-cyclohexyl-2H-pyrazol-3-ol (0.29 g, 0.88 mmol) and sodium hydride (50 mg, 1.25 mmol of a 40% suspension in mineral oil) were stirred in THF-DMF (1:1) (10 mL) at 0° C. for 0.5 h, then allowed to warm to room temperature. Dimethyl sulphate (0.1 mL, 1 mmol) was added and the mixture stirred overnight. After concentration in vacuo, the mixture was poured into water (10 mL) and extracted with EtOAc (20 mL). The organic layer was separated washed with water (2×10 mL) and dried (MgSO$_4$). Filtration and evaporation of the solvent afforded a yellow oil, which was purified by chromatography with EtOAc-hexane (1:1) as eluant. (0.24 g, 81%).

$^1$H NMR (CDCl$_3$) δ 5.54 (1H, s), 4.40 (2H, s), 3.96 (1H, m), 3.84 (3H, s), 2.15 (3H, br.s), 1.97–1.82 (12H, m), 1.67–1.63 (7H, m), 1.37–1.24 (m, 3H).

Step b. 3-(Adamantan-1-yloxymethyl)-4-bromo-1-cyclohexyl-5-methoxy-1H-pyrazole 3-(Adamantan-1-yloxymethyl)-1-cyclohexyl-5-methoxy-1H-pyrazole (0.24 g, 0.7 mmol), azobisisobutyronitrile (2 mg) and N-bromosuccinimide (0.14 g, 0.8 mmol) were stirred in CCl$_4$ (10 mL) for 1 h under illumination (100 W light source). After filtration, the filtrate was concentrated in vacuo to afford a yellow oil. (0.3 g, 100%)

$^1$H NMR (CDCl$_3$) δ 4.36 (2H, s), 4.03–4.01 (4H, m), 2.14 (3H, br.s), 1.86–1.61 (19H, m), 1.33–1.26 (3H, m).

Step c. 3-{[3-(Adamantan-1-yloxymethyl)-1-cyclohexyl-5-methoxy-1H-pyrazole-4-carbonyl]-amino}-benzoic acid ethyl ester The compound was prepared by treating 3-(adamantan-1-yloxymethyl)-4-bromo-1-cyclohexyl-5-methoxy-1H-pyrazole with n-butyl lithium and 3-ethoxycarbonylphenyl isocyanate as outlined in Reaction Scheme 4.

$^1$H NMR (CDCl$_3$) δ 10.22 (1H, s), 8.09 (2H, d), 7.77 (1 h, d), 7.42 (1H, t), 4.66 (2H, s), 4.38 (2H, q), 4.12 (4H, m), 2.18 (3H, br.s), 1.91–1.64 (22H, m), 1.25 (6H, t).

Step d. 3-{[3-(Adamantan-1-yloxymethyl)-1-cyclohexyl-5-methoxy-1H-pyrazole-4-carbonyl]-amino}-benzoic acid The compound was prepared by the same procedure used in the preparation of Example 3, except that 3-{[3-(adamantan-1-yloxymethyl)-1-cyclohexyl-5-methoxy-1H-pyrazole-4-carbonyl]-amino}-benzoic acid ethyl ester was used in step c in place of 3-{[3-(adamantan-1-yloxymethyl)-5-hydroxy 1-o-tolyl-1H-pyrazole-4-carbonyl]-amino}-benzoic acid ethyl ester.

$^1$H NMR (DMSO-d$_6$) δ 12.92 (1H, br.s), 10.07 (1H, s), 8.20 (1H, s), 7.88 (1H, d), 7.63 (1H, s), 7.46 (1H, t), 4.54 (2H, s), 4.11 (1H, m), 4.00 (3H, s), 2.05 (3H, br.s), 1.79–1.21

(22H, m). MS (EI, MeOH), 507 (M+, 3%), 372 (M+,-Ad, 12%) calcd. 507 for $C_{29}H_{37}N_3O_5$.

EXAMPLE 6

Reaction Scheme 5

Step a. 5-(Adamantan-1-yloxymethyl)-4-bromo-2-cyclohexyl-1,2-dihydro-pyrazol-3-one A $CCl_4$ solution (10 mL) of 5-(adamantan-1-yloxymethyl)-2-cyclohexyl-2H-pyrazol-3-ol (0.11 g, 0.33 mmol), azobisisobutyronitrile (2 mg) and N-bromosuccinimide (70 mg, 0.4 mmol) was irradiated by a 100 W light source for 0.3 h at rt. After filtration to the filtrate was concentrated in vacuo to afford a crude product as a purple solid, which was purified by chromatography with EtOAc-DCM (1:4) as eluant. The product was obtained as a white glassy solid (65 mg, 48%).

$^1$H NMR (CDCl$_3$) δ 4.89 (1H, s), 4.18 (2H, m), 3.96 (1H, m), 2.19 (3H, br.s), 1.84–1.26 (22H, m).

$^1$H NMR (DMSO-d$_6$) δ 10.9 (1H, br.s), 4.18 (2H, s), 4.04 (1H, m), 2.09 (3H, br.s), 1.79–1.30 (22H, m).

Step b. 5-(Adamantan-1-yloxymethyl)-4bromo-2-cyclohexyl-1-methyl-1,2-dihydropyrazol-3-one The compound was prepared by treating 5-(adamantan-1-yloxymethyl)-4-bromo-2-cyclohexyl-1,2-dihydro-pyrazol-3-one with sodium hydride and methyl iodide as outlined in Reaction Scheme 5.

$^1$H NMR (CDCl$_3$) δ 11.01 (1H, s), 8.15–8.08 (2H, m), 7.73 (1H, d), 7.35 (1H, t), 5.15 (2H, s), 4.36 (2H, q), 4.08 (1H, m), 3.71 (3H, s), 2.25 (5H, m), 1.97–1.64 (17H, m), 1.40–1.27 (6H, m).

Step c. 3-{[5-(Adamantan-1-yloxymethyl)-2-cyclohexyl-1-methyl-3-oxo-2,3-dihydro-1H-pyrazole-4-carbonyl]-amino}-benzoic acid The compound was prepared by the same procedure used in the preparation of Example 5, except that 3-{[5-(adamantan-1-yloxymethyl)-2-cyclohexyl-1-methyl-3-oxo-2,3-dihydro-1H-pyrazole-4-carbonyl]-amino}-benzoic acid ethyl ester was used in step c in place of 3-{[3-(adamantan-1-yloxymethyl)-1-cyclohexyl-5-methoxy-1H-pyrazole-4-carbonyl]-amino}-benzoic acid ethyl ester $^1$H NMR (DMSO-d$_6$) δ 12.92 (1H, br.s), 11.20 (1H, s), 8.27 (1H, s), 7.72 (1H, d), 7.61 (1H, s), 7.42 (1H, t), 5.00 (2H, s), 4.13 (1H, m), 3.67 (3H, s), 2.05 (5H, m), 1.79–1.18 (20H, m). MS (EI, MeOH), 507 (M+, 1%), 372 (M+,-Ad, 20%) calcd. 507 for $C_{29}H_{37}N_3O_5$.

The compounds of the examples were tested for gastrin (CCK$_2$) antagonist activity in an immature rat stomach assay. The procedure was as follows:

The oesophagus of immature rats (33–50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing $3 \times 10^{-8}$ M 5-methylfurmethide, maintained at 37° and gassed vigorously with 95% $O_2$/5% $CO_2$. The stomach was continuously perfused at a rate of 1 ml min$^{-1}$ with unbuffered solution gassed with 100% $O_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et al., Br. J. Pharmacol., 1985, 86, 581.

The results obtained at gastrin (CCK$_2$) receptors are set out in Table 1.

TABLE 1

| Example | Rat Stomach pK$_B$ |
| --- | --- |
| 2 | 5.66 ± 0.24 |
| 3 | 7.72 ± 0.20 |
| 4 | 7.51 ± 0.30 |
| 5 | 6.77 ± 0.38 |
| 6 | 6.57 ± 0.30 |

It is found that the compositions and products of the present invention comprising a compound of formula (I) and a proton pump inhibitor reduce hyperplasia, associated with administration of proton pump inhibitors. This was measured according to the following experimental protocol.

Animals and Treatment:

40 male SPF Wistar rats (200 g) were divided into 4 treatment groups and 2 strata. The treatment of the 20 rats in the second stratum started 2 weeks after the treatment of the first stratum. The design of the study was completely randomised double blind with individual blinding; all rats were placed in a separate cage. Animals had continuous access to water and food.

Animals were treated once daily during 14 days:

| | |
| --- | --- |
| Control group: | 1 ml gastrin test drug vehicle + 1 ml p.o.(gavage) 0.25% Methocel (Dow Corning) |
| PPI group: | 1 ml gastrin test drug vehicle + 1 ml p.o.(gavage) 25 mg/kg Rabeprazole in 0.25% Methocel. |
| GRA group: | 1 ml gastrin test drug + 1 ml p.o. (gavage) 0.25% Methocel |
| GRA-PPI group: | 1 ml gastrin test drug + 1 ml p.o.(gavage) 25 mg/kg Rabeprazole in 0.25% Methocel. |

Gastrin test drug made up to an appropriate dose in physiologically compatible solvent.

Preparation of Tissue:

After removal of the fundus, the stomach were rinsed with phosphate buffered saline prior to fixation with 4% formalin in Millonig buffer. After 4 hours immersion in fixative solutions at room temperature, tissue was rinsed in phosphate buffered saline (PBS), dehydrated and embedded in paraffin using the Leitz paraffin embedding station (Leitz TP 1050; Germany) dehydration module and paraffin embedding module (Leitz EG 1160; Germany).

Cross sections (3 µm thick) of the oxyntic part of the stomach were made at 3 levels, each separated by a distance of 400 µm.

Immunostaining

The following indirect immunofluorescence labeling method was used:

- removal of paraffin and rehydratation of the sections followed by a blocking step
- primary antibodies: polyclonal guinea pig anti-histidine decarboxylase, 1/2000 (from Euro-Diagnostica) and monoclonal mouse anti PCNA 1/2500 (Clone PC10 from Sigma). All antibodies were diluted in a 0.2% BSA solution. Sections were incubated overnight at 4° C. and then washed with a BSA solution.
- secondary antibodies: goat anti guinea pig coupled to CY5, 1/500 (from Jackson Laboratories) and goat anti-mouse coupled to Cy3, 1/250 (from Jackson Laboratories); incubation for 4 hours at 37° C. After rinsing with BSA and PBS solutions, sections were mounted with slowfade (Molecular Probes Europe BV), and stored at 4° C.

Imaging

Fluorescence labelling was observed with an epifluorescence microscope or a Zeiss LSM510 (Carl Zeiss Jena GmbH) confocal microscope.

By using CY5- and CY3-coupled antibodies, the high autofluorescence properties of the oxyntic mucosa were circumvented when sections are illuminated by a 488 nm (FITC channel) light source. Negative controls, by omitting the primary antibodies, and an isotype control staining for PCNA showed complete absence of staining. The specific labelling of PCNA was checked using double staining with TOPRO-3® (Molecular Probes Europe BV), a nuclear stain. Only in the most luminal located epithelial cells, non-specific cytoplasmic labelling was present. In the glandular part of the mucosa, non-specific PCNA-staining was absent.

For determination of the labelling index of ECL cells, at least 80 confocal images per rat were taken from the 3 slides at the 3 different levels. The ratio of double labelled cells (HDC+PCNA) and all HDC labelled cells yielded the labelling index of ECL cells.

Proliferation activity of ECL cells in the PPI group is expected to be increased compared with sham, GRA and GRA-PPI groups (Eissele, R., Patberg, H., Koop, H., Krack, W., Lorenz, W., McKnight, A. T., and Arnold, R. Effect of gastrin receptor blockade on endrocine cells in rats during achlorhydria. *Gastroenterology*, 103, 1596–1601, 1992). Increased proliferation by PPI will be completely blocked by GRA.

What is claimed is:

1. A compound of the formula (I), (IIa) or (IIb)

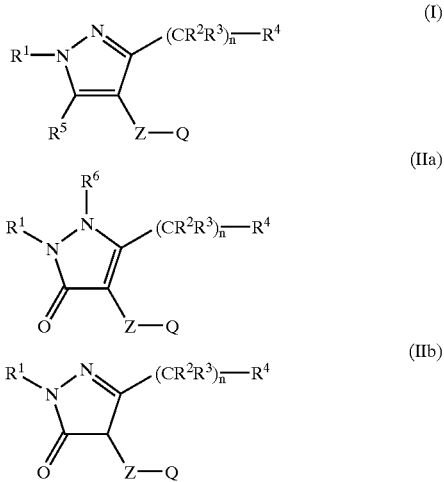

wherein n is from 1 to 4;

$R^1$ is $C_1$ to $C_{15}$ hydrocarbyl wherein up to three C atoms may optionally be replaced by an atom independently selected from the group consisting of N, O, and S, and up to three H atoms may optionally be replaced by halogen atoms;

$R^2$ is selected from the group consisting of H, Me, Et, Pr and OH, each $R^2$ being independently selected from the group consisting of H, Me, Et, Pr and OH when n is greater than 1;

$R^3$ is selected from the group consisting of H, Me, Et and Pr when n is 1; or, when n is greater than 1, each $R^3$ is independently selected from the group consisting of H, Me, Et and Pr, or two $R^3$ groups on neighbouring carbon atoms are linked to form a $C_3$ to $C_6$ carbocylic ring, or two $R^3$ groups are absent from neighbouring carbon atoms which are linked by a double bond; or $R^2$ and $R^3$ on the same carbon atom together represent an =O group;

$R^4$ is $C_1$ to $C_{15}$ hydrocarbyl wherein up to two C atoms may optionally be replaced by an atom independently selected from the group of N, O, and S and up to three H atoms may optionally be replaced by halogen atoms;

$R^5$ is H, OH or $C_1$ to $C_{15}$ hydrocarbyl wherein up to two C atoms may optionally be replaced by an atom independently selected from the group consisting of N, O, and S and up to three H atoms may optionally be replaced by halogen atoms;

$R^6$ is H or $C_1$ to $C_{15}$ hydrocarbyl wherein up to two C atoms may optionally be replaced by an atom independently selected from the group consisting of N, O, and S and up to three H atoms may optionally be replaced by halogen atoms;

Z is selected from the group consisting of: —$(NR^7)_a$—CO—$(NR^8)_b$—, (wherein a is 0 or 1, b is 0 or 1, and $R^7$ and $R^8$ are independently selected from the group consisting of H, Me, Et, Pr or Bn; —CO—$NR^7$—$CH_2$—CO—$NR^8$—; —CO—O—; —$CH_2$—$CH_2$—; —CH=CH—; —$CH_2$—$NR^8$—; and a bond;

Q is —$R^9$V, or

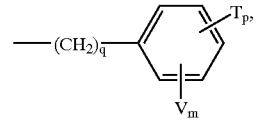

wherein $R^9$ is —$CH_2$—; —$CH_2$—$CH_2$—; or

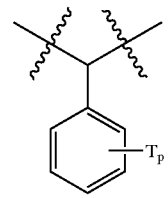

or $R^9$ and $R^8$, together with the nitrogen atom to which $R^8$ is attached, form a piperidine or pyrrolidine ring which is substituted by V;

V is selected from the group consisting of —CO—NH—$SO_2$-Ph, —$SO_2$—NH—CO-Ph, and a group of the formula —$R^{10}U$, wherein U is selected from the group consisting of —COOH, tetrazolyl, —CONHOH— or —$SO_3H$; and $R^{10}$ is selected from the group consisting of a bond; $C_1$ to $C_6$ hydrocarbylene, optionally substituted by hydroxy, amino or acetamido; —O—($C_1$ to $C_3$ alkylene)-; —$SO_2NR^{11}$—$CHR^{12}$—; —CO—$NR^{11}$—$CHR^{12}$—, wherein $R^{11}$ and $R^{12}$ are independently selected from H and methyl; or —NH—(CO)$_c$—$CH_2$—, c being 0 or 1;

T is selected from the group consisting of $C_1$ to $C_6$ hydrocarbyl, —$NR^7R^8$ (wherein $R^7$ and $R^8$ wherein $R^7$ and $R^8$ are as defined above, —OMe, —OH, —$CH_2OH$, halogen and trihalomethyl;

m is 1 or 2;
p is from 0 to 3; and
q is from 0 to 2, with the proviso that q is 1 or 2 when Z is a bond;
or a pharmaceutically acceptable salt thereof.

2. A compound according to claim 1 wherein Q is

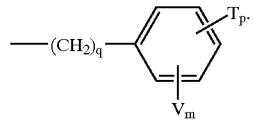

3. A compound according to claim 2 wherein Q is

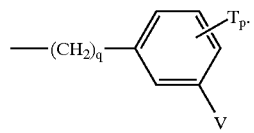

4. A compound according to claim 1, wherein $R^1$ is $C_1$ to $C_{12}$ hydrocarbyl, wherein one C atom may optionally be replaced by N or O and up to three H atoms may optionally be replaced by F, Cl or Br.

5. A compound according to claim 1, wherein $R^1$ is a moiety selected from the group consisting of $C_3$ to $C_{12}$ alicyclic; phenyl, pyridyl, phenyl $C_1$–$C_3$ alkyl or pyridyl $C_1$–$C_3$ alkyl each moiety being optionally substituted with OMe, $NMe_2$, $CF_3$, Me, F, Cl, Br or I; or $R^1$ is $C_1$ to $C_8$ alkyl.

6. A compound according to claim 1, wherein $R^5$ is H, OH or $C_1$ to $C_{12}$ hydrocarbyl wherein one C atom may optionally be replaced by N or O and up to three H atoms may optionally be independently replaced by F, Cl, or Br.

7. A compound according to claim 1, wherein $R^5$ is selected from the group consisting of H; OH; $C_3$ to $C_{12}$ alicyclic; $C_3$ to $C_{12}$ alicyclic; $C_1$ to $C_8$ alkyl; and $C_1$ to $C_8$ alkoxy, or $R^5$ is a moiety selected from the group consisting of phenyl, pyridyl, phenyl $C_1$–$C_3$ alkyl, phenyl $C_1$–$C_3$ alkoxy, pyridyl $C_1$–$C_3$ alkyl, or pyridyl $C_1$–$C_3$ alkoxy wherein each moiety is optionally substituted with OMe, $NMe_2$, $CF_3$, Me, F, Cl, Br or I.

8. A compound according to claim 1, wherein $R^6$ is H or $C_1$ to $C_{12}$ hydrocarbyl wherein one C atom may optionally be replaced by N or O and up to three H atoms may optionally be independently replaced by F, Cl, or Br.

9. A compound according to claim 1, wherein $R^6$ is H or $C_1$ to $C_8$ alkyl; or $R^6$ is a moiety selected from the group consisting of $C_3$ to $C_{12}$ alicyclic; phenyl, pyridyl, phenyl $C_1$–$C_3$ alkyl or pyridyl $C_1$–$C_3$ alkyl, wherein each moiety is optionally substituted with OMe, $NMe_2$, $CF_3$, Me, F, Cl, Br or I.

10. A compound according to claim 1, wherein Z is —CO—NH—.

11. A compound according to claim 1, wherein p is 0 or 1, and q is 0.

12. A compound according to claim 1, wherein T is $C_1$ to $C_6$ hydrocarbyl or halo.

13. A compound according to claim 1, wherein V is —$CO_2H$, —$CH_2CO_2H$ or tetrazolyl.

14. A compound according to claim 1, wherein $R^2$ and $R^3$ are H, and n is from 1 to 3.

15. A compound according to claim 1 wherein $R^2$ and $R^3$ together form an =O group, and n is 1.

16. A compound according to claim 14 or claim 15 wherein $R^4$ is $C_3$ to $C_{12}$ carbocyclic.

17. A compound according to claim 16 wherein $R^4$ is adamantyl, cycloheptyl, cyclohexyl or phenyl.

18. A compound according to claim 14 or claim 15 wherein $R^4$ is —NH—$R^{13}$ or —$OR^{13}$, wherein $R^{13}$ is $C_3$ to $C_{12}$ carbocyclic.

19. A compound according to claim 18 wherein $R^{13}$ is adamantyl, cycloheptyl, cyclohexyl or phenyl.

20. A compound according to claim 1 wherein Z is —$(NR^7)_a$—CO—$(NR^8)_b$—, —CO—NH—$CH_2$—CO—NH— or a bond; Q is

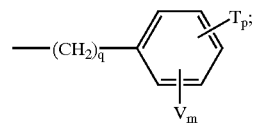

V is —CO—NH—$SO_2$-Ph, —$SO_2$—NH—CO-Ph, —$OCH_2COOH$, tetrazolyl or —$(CH_2)_s COOH$, wherein s is from 0 to 2; and T is $C_1$ to $C_6$ hydrocarbyl, —$NR^8R^8$, —OMe, —OH, —$CH_2OH$ or halogen.

21. A compound according to claim 1 wherein Z is —$(NR^7)_a$—CO—$(NR^8)_b$—, Q is —$(CH_2)_r COOH$, wherein r is from 1 to 3; and T is $C_1$ to $C_6$ hydrocarbyl, —$NR^7R^8$, —OMe, —OH, —$CH_2OH$ or halogen.

22. A compound according to claim 1 wherein -Z-Q is

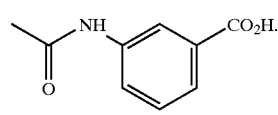

23. A compound which is degraded in vivo to yield a compound according to claim 1.

24. A method of making a compound of formula (I) wherein $R^5$ is H, comprising the step of reacting a compound of formula (IV), or a suitably protected derivative thereof, with $R^7NHNH_2$ in the presence of a base

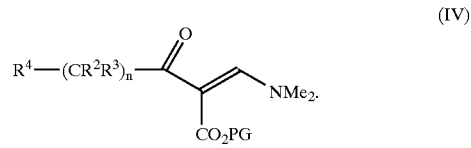

(IV)

25. A method of making a compound of formula (I) wherein $R^5$ is $C_3$ to $C_{12}$ alicyclic; phenyloptionally substituted with OMe, $NMe_2$, $CF_3$, Me, F, Cl, Br, I or OH; or $R^5$ is $C_1$ to $C_8$ alkyl, comprising the step of reacting a compound of formula (VII), or a suitably protected derivative thereof, with $R^7NHNH_2$ in the presence of a base

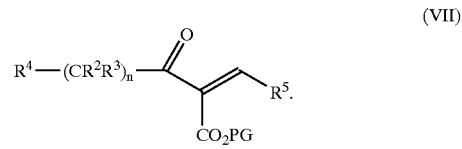

(VII)

26. A method of making a compound of formula (I) wherein $R^5$ is OH or a compound of formula (IIa) or (IIb), comprising the step of reacting a compound of formula (III), or a suitably protected derivative thereof, with R⁷NHNH₂ in the presence of a base

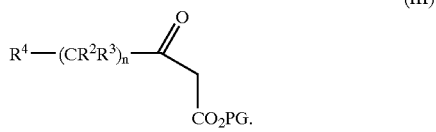

(III)

27. A pharmaceutical composition comprising a compound according to claim 1 together with a pharmaceutically acceptable diluent or carrier.

28. A pharmaceutical composition comprising a proton pump inhibitor and a compound according to claim 1 together with a pharmaceutically acceptable diluent or carrier.

29. A composition according to claim 28 wherein the proton pump inhibitor is selected from (RS) rabeprazole, (RS)-omeprazole, lansoprazole, pantoprazole, (R)-omeprazole, (S)-omeprazole, perprazole, (R)-rabeprazole, (S)-rabeprazole, or the alkaline salts thereof.

30. A method of making a pharmaceutical composition comprising mixing a compound according to claim 1 with a pharmaceutically acceptable diluent or carrier.

31. A method of making a pharmaceutical composition according to any claim 28, comprising mixing a compound of formula (I), IIa or IIb and a proton pump inhibitor with a pharmaceutically acceptable diluent or carrier.

32. A method of treating or alleviating the symptoms of a gastrointestinal disorder, comprising administering to a patient suffering from said disorder a therapeutically beneficial amount of a composition according to claim 28.

33. The method according to claim 32 wherein said composition provides a synergistic effect on said gastrointestinal disorder in said patient, and wherein said synergistic effect is reduction of acid secretion, prevention of a gastrointestinal disorder, or the reduction of one or more adverse effects associated with one of the active ingredients of said composition by the other active ingredients.

34. The method according to claim 32, wherein the amount of each of the active ingredients is equal to or less than that which is approved or indicated in monotherapy with said active ingredient.

35. A method of treating or alleviating the symptoms of a gastrointestinal disorder, comprising administering to a patient suffering from said disorder a therapeutically beneficial amount of a proton pump inhibitor and a compound according to claim 1, wherein said protein pump inhibitor and said compound are administered simultaneously, separately or sequentially.

36. A method of treating or alleviating the symptoms of a gastrointestinal disorder, comprising administering to a patient suffering from said disorder a therapeutically beneficial amount of a compound according to claim 1.

37. A method of treating or alleviating the symptoms of a gastrin-related disorder, comprising administering to a patient suffering from said disorder a therapeutically beneficial amount of proton pump inhibitor and a compound according to claim 1, wherein said proton pump inhibitor enhances the effect of said compound.

38. The method according to claim 37, wherein said proton pump inhibitor and said compound are administered simultaneously or sequentially, and wherein said compound enhances the effect of said proton pump inhibitor on the reduction of acid secretion.

39. The method according to claim 37, wherein said proton pump inhibitor and said compound are administered simultaneously or sequentially, and wherein said compound reduces an adverse effect associated with administration of proton pump inhibitors.

40. The method according to claim 39, wherein said adverse effect is hyperplasia.

* * * * *